(12) United States Patent
Golobek

(10) Patent No.: US 7,008,429 B2
(45) Date of Patent: Mar. 7, 2006

(54) BIO-ABSORBABLE BONE TIE WITH CONVEX HEAD

(76) Inventor: Donald D. Golobek, 70 Meade St., Wellsboro, PA (US) 16901

( * ) Notice: Subject to any disclaimer, the term of this patent is extended or adjusted under 35 U.S.C. 154(b) by 0 days.

(21) Appl. No.: 10/873,135

(22) Filed: Jun. 23, 2004

(65) Prior Publication Data
US 2005/0288674 A1    Dec. 29, 2005

(51) Int. Cl.
A61F 5/04    (2006.01)
A65D 63/06    (2006.01)
(52) U.S. Cl. .................................. 606/74; 24/30.5 P
(58) Field of Classification Search .............. 606/60, 606/72, 74, 77, 103, 139, 148, 151, 157, 606/230; 24/30.5 P, 16 PB, 16 R, 17 AP
See application file for complete search history.

(56) References Cited

U.S. PATENT DOCUMENTS

| | | | | |
|---|---|---|---|---|
| 3,570,497 A | * | 3/1971 | Lemole | ....................... 606/151 |
| 3,672,003 A | * | 6/1972 | Morgan | ..................... 24/16 PB |
| 3,872,547 A | * | 3/1975 | Caveney et al. | ........... 24/16 PB |
| 4,097,966 A | * | 7/1978 | Lefnaer | ...................... 24/16 PB |
| 4,119,091 A | * | 10/1978 | Partridge | ..................... 606/74 |
| 4,138,770 A | * | 2/1979 | Barrette et al. | ........... 24/16 PB |
| 4,183,119 A | * | 1/1980 | Stewart et al. | ............. 24/16 PB |
| 4,272,900 A | * | 6/1981 | MacLarty et al. | .............. 40/665 |
| 4,413,380 A | * | 11/1983 | Suzuki | ...................... 24/16 PB |
| 4,535,764 A | | 8/1985 | Ebert | |
| 4,606,335 A | | 8/1986 | Wedeen | |
| 4,730,615 A | * | 3/1988 | Sutherland et al. | .......... 606/215 |
| 4,813,416 A | | 3/1989 | Pollak | |
| 4,966,143 A | * | 10/1990 | Meinershagen | .............. 606/103 |
| 5,356,417 A | | 10/1994 | Golds | |
| 5,462,542 A | | 10/1995 | Alesi, Jr. | |
| 5,810,854 A | * | 9/1998 | Beach | ......................... 606/151 |
| 5,851,209 A | | 12/1998 | Kummer et al. | |
| 6,513,202 B1 | * | 2/2003 | Zimmermann | ........... 24/30.5 R |

* cited by examiner

Primary Examiner—Eduardo C. Robert
Assistant Examiner—David Comstock
(74) Attorney, Agent, or Firm—Richard C. Litman

(57) ABSTRACT

The bio-absorbable bone tie with convex head is an elongated band having a convex head portion and is used for securing fragments of a fractured bone together. The elongated band portion includes a plurality of notches defined therein. The convex head portion has a convex shape with smooth, rounded edges and includes a channel or slot to receive a segment of the elongated band portion. At least one lock tooth extends into the channel or slot to engage the notches in the band and prevent the band from slipping back out of the channel, similar to a ratchet and pawl mechanism. The bone tie is constructed of a bio-absorbable material, such as polylactic acid. The leading end of the bone tie is the same color as the receiving opening of a corresponding inserter tool to minimize confusion when installing the bone tie with the inserter tool.

10 Claims, 4 Drawing Sheets

BIO-ABSORBABLE BONE TIE WITH CONVEX HEAD

BACKGROUND OF THE INVENTION

1. Field of the Invention

The present invention relates to surgical devices for securing a fractured bone while the bone is healing, and more particularly, to a bio-absorbable bone tie with a convex head portion that minimizes chaffing and abrasion of soft tissue. The bone tie is bio-absorbable to eliminate the need for surgery for its removal, and includes a color-coded leading end to facilitate use with a corresponding inserter tool.

2. Description of the Related Art

When treating a severely fractured large bone, a surgeon often must secure fragments of the bone together to enable the bone to heal properly. Typically, the fragments are secured together by either threading one or more metal screws through the fragments or by tightly looping a segment of wire or an elongated band around the fragments. However, a notable drawback of securing bone fragments with metal screws, wire or a metal band is that removal of those items requires surgery, a procedure most patients would prefer to avoid. Additionally, securing bone fragments with a loop of wire or an elongated band often requires the time-consuming use of a tensioning device, and generally results in chaffing and abrasion of the soft tissue surrounding the closing mechanism of the loop or band. Furthermore, the use of an inserter tool when installing wire or a band can lead to confusion as to which opening in the tool should receive the leading end of the wire or band.

As a result, a need exists for a means of securing bone fragments together that eliminates the need for removal surgery, that incorporates a closing mechanism that minimizes chaffing and abrasion of soft tissue, that can be installed without the use of time-consuming tensioning devices, and that is configured to eliminate confusion as to which inserter tool opening should receive the means.

U.S. Pat. No. 4,535,764, issued Aug. 20, 1985 to E. A. Ebert, describes a surgical bone tie constructed of a metal band with an integrated needle at one end and a flat, edged locking mechanism at the other end. U.S. Pat. No. 4,606,335, issued Aug. 19, 1986 to R. S. Wedeen, describes a cerclage wire passer that includes an S-shaped head with an eyelet at one end and a handle extending from the other end. The device is used to loop wire around a human bone.

U.S. Pat. No. 4,730,614, issued Mar. 15, 1988 to L. A. Sutherland, describes a sternum closure device constructed of metal with a box-shaped head portion. U.S. Pat. No. 4,813,416, issued Mar. 21, 1989 to S. B. Pollak, describes a bonding assembly for sternum closing that includes a metallic band with a surgical needle extending from one end and a buckling mechanism at the other end.

U.S. Pat. No. 5,356,417, issued Oct. 18, 1994 to E. Golds, describes an absorbable sternum closure buckle that includes a strap and a two-piece buckle member. The two pieces of the buckle member are attached to different segments of the strap and are constructed of a bio-absorbable material. The strap is formed into a loop when the buckle is latched together.

U.S. Pat. No. 5,462,542, issued Oct. 31, 1995 to T. W. Alesi, Jr., describes a sternum buckle with serrated strap that includes an elongated strap with a box-shaped buckle member constructed of a bio-absorbable material. U.S. Pat. No. 5,851,209, issued Dec. 22, 1998 to F. J. Kummer, et al., describes a bone cerclage tool for encircling a bone with wire that includes a curved tube attached to a handle.

None of the above inventions and patents, taken either singly or in combination, is seen to describe the instant invention as claimed. Thus a bio-absorbable bone tie with convex head solving the aforementioned problems is desired.

SUMMARY OF THE INVENTION

The bio-absorbable bone tie with convex head is an elongated band having a convex head portion and is used for securing fragments of a fractured bone together. The elongated band portion includes a plurality of notches defined therein. The convex head portion has a convex shape with smooth, rounded edges and includes a channel or slot to receive a segment of the elongated band portion. At least one lock tooth extends into the channel or slot to engage the notches in the band and prevent the band from slipping back out of the channel, similar to a ratchet and pawl mechanism. The bone tie is constructed of a bio-absorbable material, such as polylactic acid. The leading end of the bone tie is the same color as the receiving opening of a corresponding inserter tool to minimize confusion when installing the bone tie with the inserter tool.

The bone tie is absorbed into the body within eighteen to twenty-four months to avoid the need for removal surgery, and is installed without use of a time-consuming tensioning device. The smooth convex head minimizes chaffing and abrasion of tissue surrounding the head portion.

Accordingly, it is a principal object of the invention to provide a bio-absorbable bone tie for securing fragments of a bone together to enable proper healing of the bone.

It is another object of the invention to provide a bone tie for securing the fragments of a bone together that is constructed of a bio-absorbable material, preferably polylactic acid, in order to eliminate the need for removal surgery.

It is a further object of the invention to provide a bone tie for securing fragments of a bone together that employs a convex head as part of its closing mechanism to thereby avoid chaffing and abrasion of surrounding soft tissue.

Still another object of the invention is to provide a bio-absorbable bone tie for securing fragments of a bone together that can be installed without the use of a time-consuming tensioning tool.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 5:
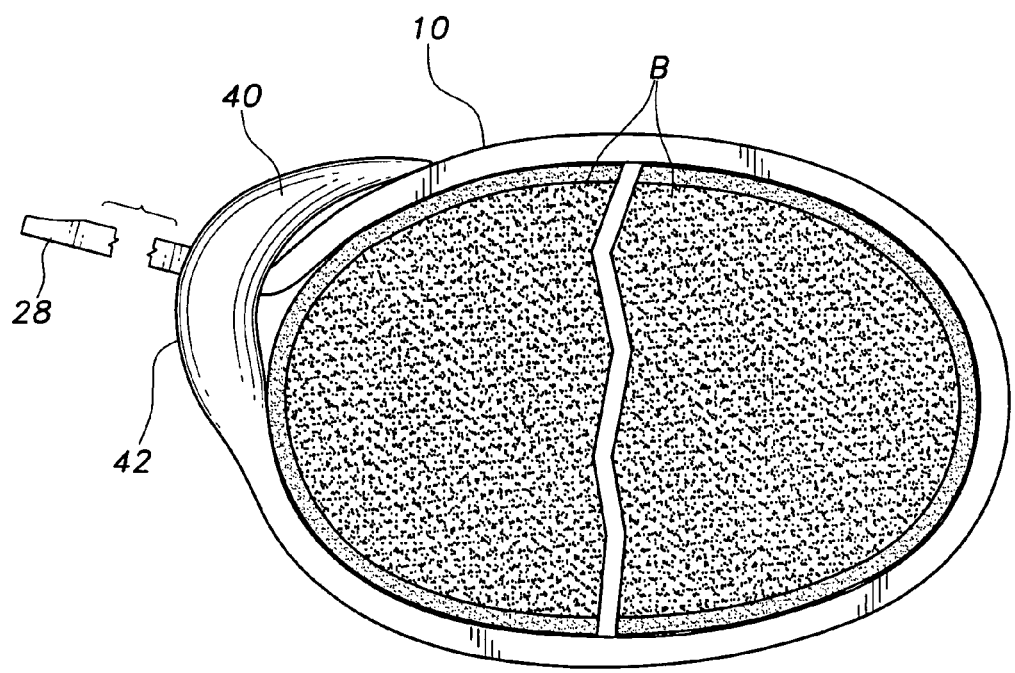
FIG. 5 is an environmental side view of a bio-absorbable bone tie with convex head according to the present invention shown securing fragments of a fractured bone together.

The present invention is a bio-absorbable bone tie with convex head, designated generally as 10 in the drawings. As shown in FIG. 5, the bone tie 10 is adapted to secure fragments of a fractured bone B together without presenting a square edge or protrusion into the surrounding soft tissue.

Figure 1:
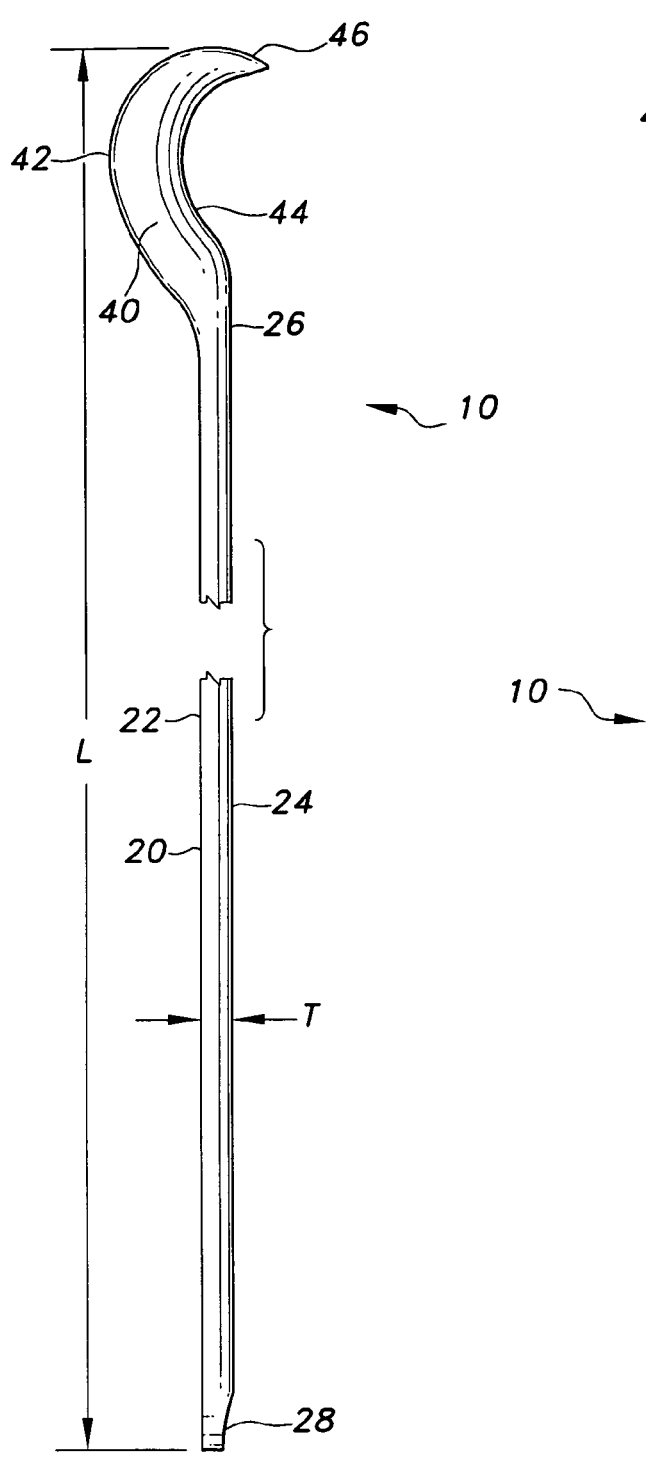
FIG. 1 is a fragmented, side view of a bio-absorbable bone tie with convex head according to the present invention.
Figure 2:
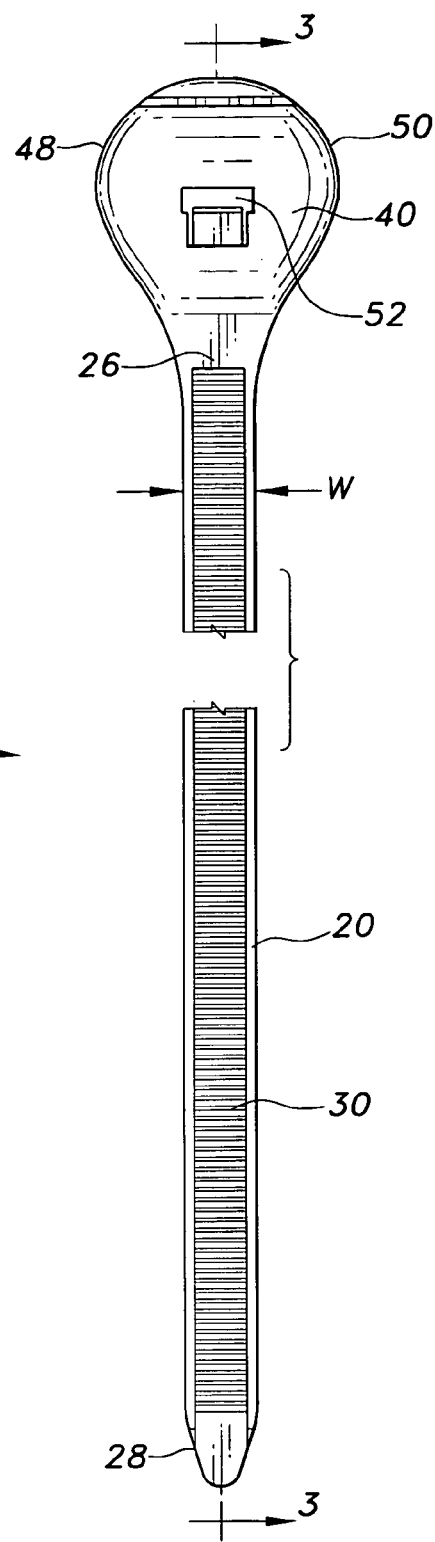
FIG. 2 is a fragmented, front view of a bio-absorbable bone tie with convex head according to the present invention.
Figure 3:
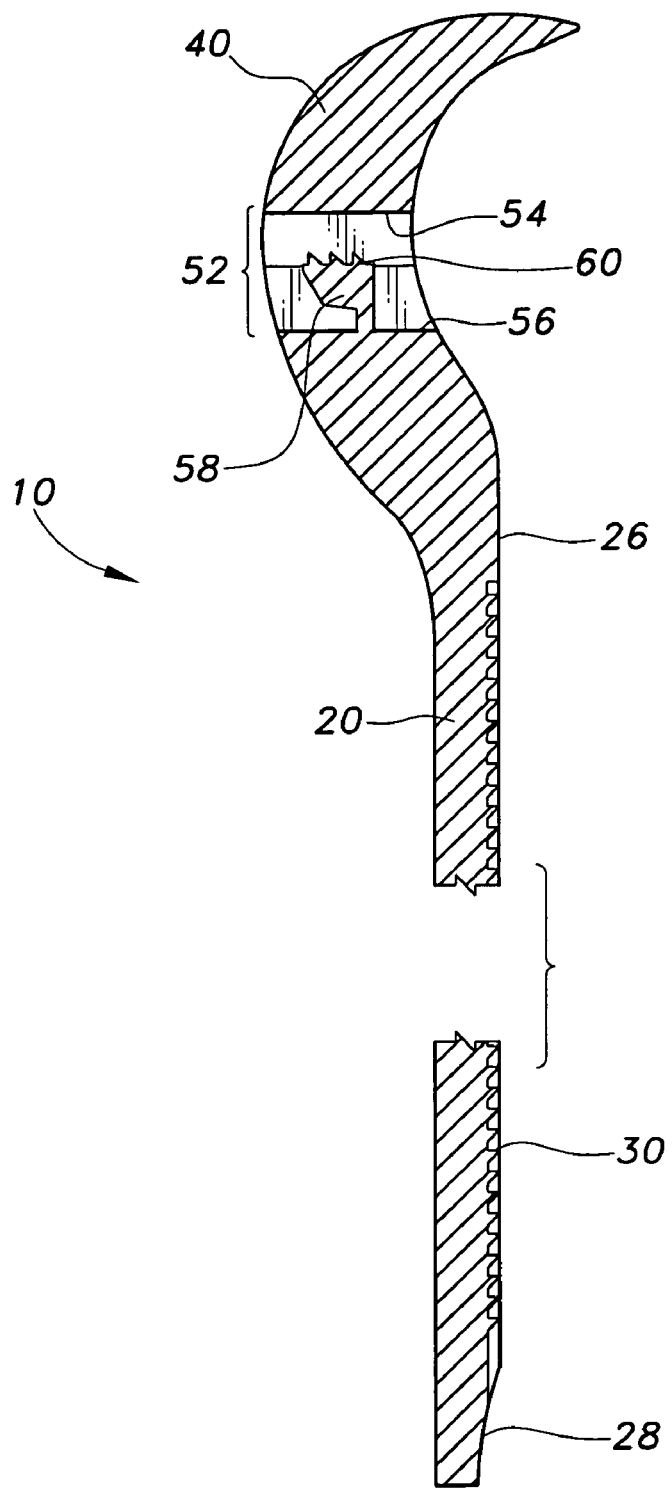
FIG. 3 is a section view along lines 3—3 of FIG. 2.

Referring to FIGS. 1, 2 and 3, the bone tie 10 includes an elongated band portion 20 and a head portion 40. The elongated band portion 20 is a flat band with two sides 22 and 24, a leading end 28 and a trailing end 26. The front side 24 of the band 20 has a plurality of notches 30 extending substantially from the leading end 28 to the trailing end 26. The notches 30 are uniformly spaced and are adapted to interlock with at least one lock tooth 60 or detent tongue of a lock member 58. Each notch 30 runs transversely across the width W of the band 20. The leading end 28 is tapered and is the same color as the distal end 102 of the corresponding inserter tool 100. The trailing end 26 is attached to the head portion 40.

The head portion 40 extends from the elongated band portion 20 and has a front side 44, a rear side 42, a tip 46 and two lateral sides 48 and 50. The front side 44 of the head 40 is concave and the bottom side 42 is convex, the head 40 being somewhat spoon-shaped. The lateral sides 48 and 50 form smooth rounded edges. A substantially rectangular channel or slot 52 dimensioned for receiving the elongated band portion 20 extends from the through the head portion 40. The channel 52 is defined by a top wall 54, a bottom wall 56 and two sidewalls. The entrance to the channel 52 is the opening on the topside 44 of the head portion 40 and the exit from the channel 52 is the opening on the bottom side 42 of the head portion 40. A lock member 58 is mounted to the bottom wall 56 of the channel 52 and is adapted to interlock with the notches 30 of the elongated band portion 20 when the band 20 is fed into the channel 52 entrance. The lock member 58 includes at least one lock tooth 60 (a plurality of lock teeth 60 being shown in FIG. 3) that interlock with the notches 30 similar to a ratchet and pawl mechanism, so that the band 20 can only move in one direction, toward the exit of the channel 52. This may be accomplished by shaping the lock teeth 60 to ramp upward from the entrance to the exit side of the channel 52, while the opposite face of the teeth 60 slope back toward the entrance or drop vertically, as shown in FIG. 3, or in any other manner known in the art of locking ties. Hence, once the lock member 58 has engaged the notches 30, the band 20 cannot move in the direction from the exit toward the entrance of the channel 52 and therefore cannot be removed from the channel 52.

The bone tie 10 is constructed of a bio-absorbable material, such as polylactic acid, that is absorbed or resorbed in the body, and has an overall length L of 120 millimeters, a thickness T of 1.5 millimeters and a width W of 3.0 millimeters. In an alternative embodiment, the bone tie 10 has an overall length L of 360 millimeters, a thickness T of 2.0 millimeters and a width W of 5.0 millimeters. Alternatively, the bone tie 10 is constructed of a biodegradable polymer or copolymer of glycolide, lactide trimethylene, carbonate, lactone, dioxanone or caprolactone.

Figure 4:
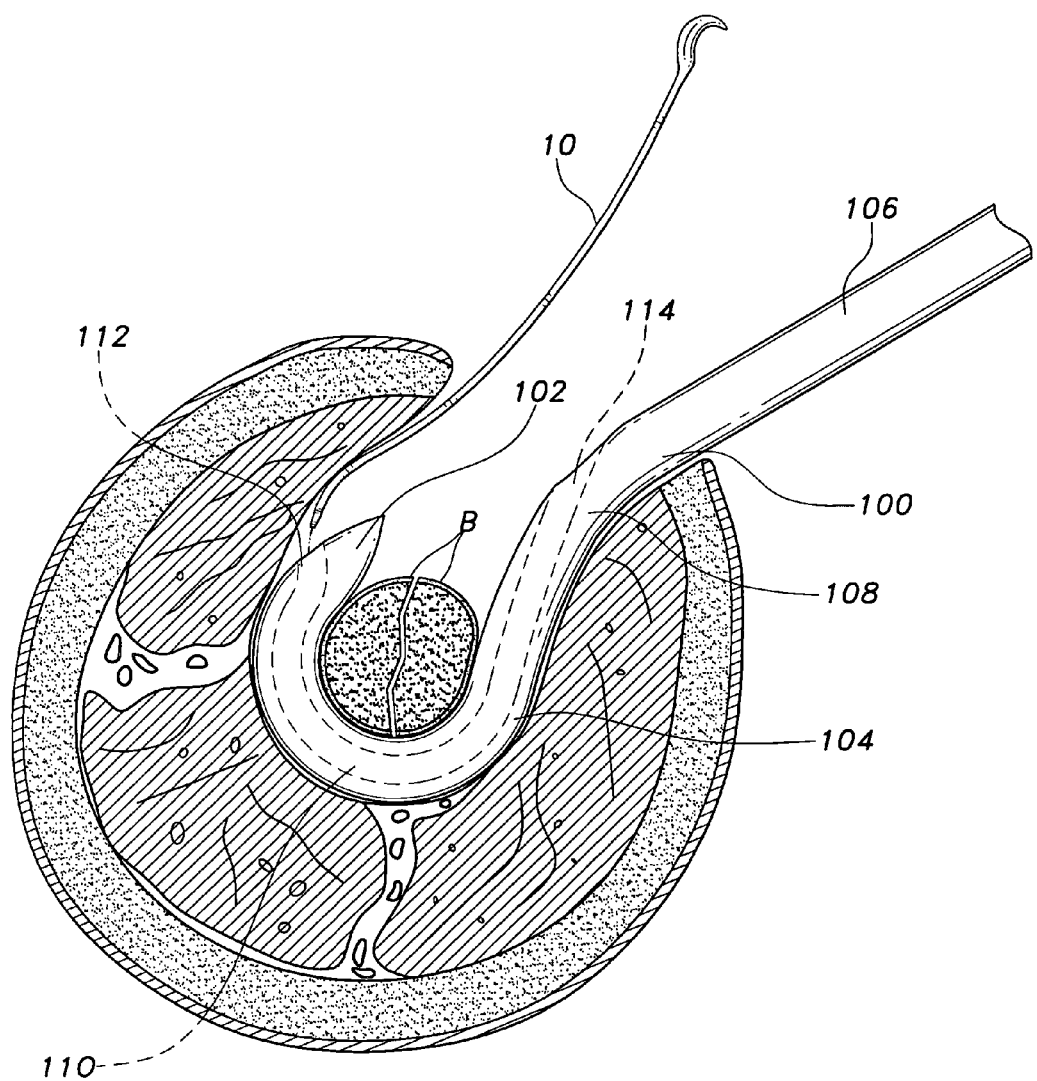
FIG. 4 is a diagrammatic, environmental side view of a bio-absorbable bone tie with convex head according to the present invention being installed around fragments of a fractured bone shown in relation to a corresponding inserter tool.

A corresponding inserter tool 100, shown in FIG. 4, is used to position the bone tie 10 around a fractured bone. The inserter tool 100 includes a substantially tubular hook portion 104 and a handle portion 106. The hook portion 104 is in the form of an arc, defines a tubular passage 110, and has a distal end 102, a proximal end 108, a first tubular passage opening 112 at the distal end 102 of the hook 104, and a second tubular passage opening 114 at the proximal end 108 of the hook 104. The tubular passage 110 extends between the first tubular passage opening 112 and the second tubular passage opening 114. The handle portion 106 extends from the proximal end 108 and is substantially cylindrical. The distal end 102 is a different color than the rest of the inserter tool 100 but is the same color as the leading end 28 of the bone tie 10. In an alternative embodiment, the distal end 102 and the leading end 28 of the bone tie 10 are imprinted with similar indicia.

The bone tie 10 is secured around a fractured bone B by first encircling the bone B with the hook portion 104 of the insert tool 100, as shown in FIG. 4. The leading end 28 of the bone tie 10 is then inserted into the first tubular passage opening 112 located on the distal end 102 of the insert tool 100 with the front side of the bone tie 10 facing toward the bone B. The leading end 28 of the bone tie 10 and the distal end 102 of the insert tool 100 are the same color in order to avoid confusion over which opening in the inserter tool 100 receives the bone tie 10. The bone tie 10 is then inserted into the tubular passage 110 until the head portion 40 is near the distal end 102 and the elongated band portion 20 extends out of the second tubular passage opening 114. With the head portion 40 held in place near the bone B, the inserter is withdrawn from the bone B. As the inserter is withdrawn, the elongated band portion 20 is exposed around the bone B. The leading end 28 of the bone tie 10 is then inserted in to the channel 52 in the head portion 40 to form a loop around the bone B, as shown in FIG. 5. The elongated band portion 20 is fed though the channel 52 until the loop formed by the bone tie 10 is an appropriate tightness. The portion of the elongated band portion 20 that extends beyond the bottom 42 surface of the bone tie 10 is then severed. The fragments of the bone B are then secured together without any protrusions or square edges extending from the bone tie 10 thereby enabling the bone B to heal properly without chaffing or abrasion of surrounding soft tissue. The body absorbs or resorbs the bone tie 10 within eighteen to twenty-four months.

It is to be understood that the present invention is not limited to the embodiments described above, but encompasses any and all embodiments within the scope of the following claims.

I claim:

1. A bio-absorbable bone tie with convex head, comprising:

an elongated, flat, flexible band having a front side, a rear side, a leading end and a trailing end, the front side having a plurality of notches defined therein;

a spoon-shaped head portion having a pair of smooth, rounded lateral edges, a front side having a concave shape, and a back side having a convex shape disposed between said lateral edges, the head being integral with and extending from the trailing end of said band, said head portion defining a channel having an entrance substantially centrally disposed in said concave shaped front side, and an exit substantially centrally disposed in said convex shaped back side, said channel extending through said head portion from the front side to the back side, the channel being dimensioned for reception of said band; and a lock member disposed within said channel having at least one lock tooth configured to interlock the notches defined in the front side of said band, thereby securing said band around bone fragments of a fractured bone when the leading end of said band is fed into the entrance of the channel in said head portion, said band, said head portion, and said lock member being formed in one piece from a bio-absorbable material;

wherein said leading end of said band is fed through said channel from said front side of said head portion, upon tensioning said band around a fragmented bone said locking member preventing said band from reversing from said channel, said head portion is firmly secured against a surface of the fragmented bone;

whereby said head portion forms a smooth rounded surface adjacent the fragmented bone, preventing any damage to tissue surrounding the fragmented bone.

2. The bio-absorbable bone tie with convex head according to claim 1, wherein said bio-absorbable material is polylactic acid.

3. The bio-absorbable bone tie with convex head according to claim 1, wherein said bio-absorbable material is a material selected from the group consisting of glycolide polymers and copolymers, lactide trimethylene, carbonate, lactone, dioxanone, and caprolactone.

4. The bio-absorbable bone tie with convex head according to claim 1, wherein said band and head portion have a combined overall length of about 120.0 millimeters, the band having a thickness of about 1.5 millimeters and a width of about 3.0 millimeters.

5. The bio-absorbable bone tie with convex head according to claim 1, wherein said band and head portion have a combined overall length of about 360.0 millimeters, the band having a thickness of about 2.0 millimeters and a width of about 5.0 millimeters.

6. The bio-absorbable bone tie with convex head according to claim 1, further comprising an inserter tool having a substantially tubular hook portion adapted for encircling a bone and having a handle portion, the hook portion being in the form of an arc defining a tubular passage and having a distal end, a proximal end, a first tubular passage opening and a second tubular passage opening, the tubular passage being dimensioned for reception of said band portion, said handle extending from the proximal end of said hook portion.

7. The bio-absorbable bone tie with convex head according to claim 6, wherein the leading end of said band and the distal end of said inserter tool are the same color.

8. A system for securing bone fractures to promote bone healing, comprising:

a bone tie formed from a bio-absorbable material, said bone tie having an elongated band, a head portion, and a locking member;

said bone tie has a front side, a rear side, a leading end and a trailing end, the front side has a plurality of notches, a head portion being designed and configured to have a spoon-shape having a pair of smooth, rounded lateral edges, a front side having a concave shape, and a back side having a convex shape disposed between said lateral edges, the head being integral with and extending from the trailing end of said band, said head portion defining a channel having an entrance substantially centrally disposed in said concave shaped front side, and an exit substantially centrally disposed in said convex shaped back side, said channel extending through said head portion from the front side to the back side, the channel being dimensioned for reception of said band, and a lock member disposed within said channel having at least one lock tooth; and a tool for inserting said bone tie, said tool having a substantially tubular hook portion and a handle portion, said hook portion including a guide channel defined therethrough;

said tool has a substantially tubular hook end, and a handle end, said hook portion is adapted for encircling a bone, said hook portion has an arcuate form and defines a tubular passage therethrough, said tubular passage has a first tubular passage opening and a second tubular passage opening, said tubular passage is dimensioned and configured for reception of said band portion of said bone tie, and said handle extending from said proximal end of said hook portion;

wherein said guide channel is designed and configured to guide said elongated band of said bone tie therethrough;

whereby said tool is disposed about a fractured bone, said elongated band is passed through said guide channel, said tool is removed while said bone tie remains disposed about the fractured bone, said bone tie is secured around the fractured bone, and said bone tie is bio-absorbed in surrounding body tissue.

9. The system according to claim 8, whereby said band is secured around bone fragments of a fractured bone when said leading end of said band is fed into said entrance of said channel in said head portion, and said lock member engages said notches, said band, said head portion, and said lock member are integrally formed from a bio-absorbable material.

10. The system according to claim 8, wherein said tool has a substantially tubular hook end, and a handle end, said hook portion is adapted for encircling a bone, said hook portion has an arcuate form and defines a tubular passage therethrough, said tubular passage has a first tubular passage opening and a second tubular passage opening, said tubular passage is dimensioned and configured for reception of said band portion of said bone tie, and said handle extending from said proximal end of said hook portion.

* * * * *